United States Patent [19]

Moyer et al.

[11] Patent Number: 4,675,604

[45] Date of Patent: Jun. 23, 1987

[54] COMPUTERIZED AND MOTORIZED ELECTROMAGNETIC FLUX LEAKAGE INTERNAL DIAMETER TUBULAR INSPECTION DEVICE

[75] Inventors: Mark C. Moyer, Missouri City; William D. Perry, San Antonio; H. Stanley Silvus, Jr., San Antonio; William C. Gibson, San Antonio; Felix N. Kusenberger, deceased, late of San Antonio, all of Tex., by Lou A. Kusenberger, heiress

[73] Assignee: Exxon Production Research Co., Houston, Tex.

[21] Appl. No.: 770,329

[22] Filed: Aug. 28, 1985

[51] Int. Cl.$^4$ ................. G01N 27/82; G01N 27/72
[52] U.S. Cl. ................. 324/220; 324/240; 324/262; 324/227
[58] Field of Search ................. 324/219–221, 324/207, 208, 229, 237, 238, 239, 240–243, 262, 226, 227, 228

[56] References Cited

U.S. PATENT DOCUMENTS

| | | | |
|---|---|---|---|
| 2,308,159 | 1/1943 | Drummond et al. | 175/183 |
| 3,205,435 | 9/1965 | Huttall | 324/220 |
| 3,209,243 | 9/1965 | Walters et al. | 324/220 |
| 3,238,448 | 3/1966 | Wood et al. | 324/220 |
| 3,419,797 | 12/1968 | Libby | 324/220 |
| 3,460,028 | 8/1969 | Beaver et al. | 324/220 |
| 3,483,466 | 12/1969 | Crouch et al. | 324/337 |
| 3,535,624 | 10/1970 | Wood | 324/337 |
| 3,539,915 | 11/1970 | Walters et al. | 324/220 |
| 4,134,067 | 1/1979 | Woodbury | 324/219 |
| 4,188,577 | 2/1980 | Mhatre | 324/220 |
| 4,203,069 | 5/1980 | Davis | 324/220 |
| 4,217,548 | 8/1980 | Furukawa et al. | 324/220 |
| 4,258,318 | 3/1981 | Furukawa et al. | 324/220 |
| 4,418,574 | 12/1983 | Flournoy | 324/220 X |
| 4,510,447 | 4/1985 | Moyer | 324/225 |

Primary Examiner—Reinhard J. Eisenzopf
Assistant Examiner—Warren S. Edmonds
Attorney, Agent, or Firm—Jeffrey M. Hoster

[57] ABSTRACT

A device for detecting defects in the bore of a tubular member. The device includes an inspection head including an electromagnet for magnetizing the internal surface of a tubular member. The device also includes a sensor or sensors to detect magnetic flux leakage indicative of a defect. The magnetic flux sensor output is sent to a control-data acquisition system concurrently with signals as to the axial and circumferential position of the defect, which are obtained by their respective encoders. The control-data acquisition system is capable of processing and displaying the data in analog and digital form.

34 Claims, 11 Drawing Figures

COMPUTERIZED AND MOTORIZED ELECTROMAGNETIC FLUX LEAKAGE INTERNAL DIAMETER TUBULAR INSPECTION DEVICE

FIELD OF THE INVENTION

This invention relates to an apparatus for detecting flaws in a tubular member by inspecting the internal surface of the tubular member.

BACKGROUND OF THE INVENTION

It is standard practice in the oil and gas industry to nondestructively inspect tubular members that are to be used in a wellbore. Failure of such tubular members may result in drilling delays, production losses, environmental damage, and destruction of drilling and production equipment.

There are two primary methods of nondestructively inspecting tubular members for use in oil and gas well operations. The most common method is the magnetic particle method, which is accomplished by magnetizing the wall of the tubular member, typically a pipe, or by providing it with a residual magnetic field and thereafter dusting fine particles of iron or iron oxide on a region of the wall. The pattern of the particles indicates whether or not there are any flaws in the wall. While this method is sometimes adequate for inspection of the exterior surface of the pipe or for the interior surface near the ends of the pipe, it is not adequate for inspecting the interior surface of the pipe over its entire length. This results from the fact that the magnetic particle inspection method requires immediate access to the area being inspected, both for dusting the iron particles on the pipe, and for visually inspecting the pipe for indication of flaws.

A second recent method for nondestructive inspection of pipes is the electromagnetic flux leakage technique. Most commonly, this technique is applied by using an apparatus in which the magnetizing means and magnetic sensing means are mounted external to the pipe. The apparatus is placed in proximity to the exterior surface of the pipe and then moved about the exterior surface for inspection. The signals from the magnetic sensing means are generally displayed in analog form, such as on a strip chart recorder. Such an apparatus is disclosed in U.S. Pat. No. 4,510,447 to M. C. Moyer, et al. The apparatus is less sensitive to flaws on the inner surface of the pipe than to flaws on the outer surface of the pipe. This is especially true for thick walled pipe.

Various other apparatus have been suggested for detecting flaws on the inner surface of a pipe. One such apparatus is disclosed in U.S. Pat. No. 2,308,159 to Drummond et al. Drummond discloses a tubing defect detector which includes a drive motor mounted for travel along rails. Attached to the motor is a long shaft at the end of which is attached a single sensor core and a single coil, which are used for detecting flaws. For inspection operations a current is applied to the pipe to produce a closed magnetic field. The drive motor is energized to rotate the attached shaft, and the core and coil attached thereto. The motor is then pulled forward on the track, thereby causing the magnetic detection apparatus to move into the pipe being inspected. If there is a flaw in the pipe, an electric current is generated in the single coil of the sensing apparatus, and then indicated on a device such as an oscilloscope.

The Drummond apparatus has certain disadvantages. The motor used to rotate the apparatus is often too large to be placed inside the pipe being inspected. Thus, the rotating drive shaft must frequently be as long as the pipe to be inspected, creating a need for a powerful motor that can be driven through the length of the pipe. The coil used for detection of magnetic flux generally indicates that a flaw is present, but no further information is collected. Thus no details as to the exact location, axial or circumferential, or severity of the flaw is available, making manual inspection and repair logistically difficult. Drummond discloses no means which allows the apparatus to be adapted for use in pipes of varied sizes.

Other apparatus for detecting flaws located on the inner surface of a pipe are disclosed in U.S. Pat. Nos. 4,217,548 issued Aug. 12, 1980 to Furukawa et al. and 4,258,318, also to Furukawa et al. Furukawa discloses an apparatus for magnetically detecting flaws on the inner surface of a pipe comprising a magnetizing assembly supported exterior to the pipe being inspected and a detecting assembly supported from a support rod which is inserted in the interior of the pipe. Because neither the magnetizing means nor the detection means is rotatable, Furukawa discloses apparatus for rotating the pipe during inspection.

Because the apparatus disclosed in both Furukawa patents magnetize pipes from the exterior of the pipes, adequate magnetization on the internal surface of the pipe cannot be ensured. This concern is especially acute regarding thick walled pipes. The pipe must be rotated, which requires significant power, and may cause severe vibration. Further, neither Furukawa patent discloses any means for detailing the axial or circumferential location, or the severity, of the flaws. Again, manual inspection and repair is logistically difficult.

SUMMARY OF THE INVENTION

The present invention is an improved apparatus and method for detecting flaws on or near the internal surface of a tubular member such as a pipe. In addition, this invention provides detailed information on the location and severity of flaws on or near the internal surface of a tubular member.

The apparatus comprises an inspection head sized so as to be insertable into the bore of a tubular member, an azimuthal encoder for determining the circumferential position of the inspection head, a longitudinal encoder for determining the position of the inspection head in relation to the longitudinal axis of the tubular member, a longitudinal motion motor for moving the inspection head bidirectionally along the longitudinal axis of the tubular member, and an electrical connection so that all data can be transmitted to a control-data acquisition system capable of receiving and processing the signal data. The inspection head includes an electromagnet and magnetic flux leakage sensors, which are rotatable, and a rotational motor.

The combined longitudinal and rotational movement of the inspection head allows the electromagnet and magnetic flux leakage sensors to move about a helical path inside the tubular member so that flaws can be detected on substantially all of the internal surface of the tubular member. The specific location of the defects can be determined by processing the signals detected by the azimuthal encoder and the longitudinal encoder.

In practicing the method of the invention, the inspection head is deployed within a tubular member. The inspection head can be adjusted for use in pipe bores of various sizes. The rotational motor powers the rotation of the portion of the inspection head including the electromagnet and the magnetic flux leakage sensors, while a magnetic flux is created by the electromagnet and the magnetic flux leakage is detected by the magnetic flux leakage sensors. Simultaneously, the azimuthal encoder is producing signal data as to the azimuthal position of the inspection head in the tubular member, and the longitudinal encoder is producing signal data as to the position of the inspection head in relation to the longitudinal axis of the inspection head. All data may then be transmitted to a control-data acquisition system for processing.

DESCRIPTION OF THE PREFERRED EMBODIMENT

The invention is an apparatus and method for detecting flaws on or near the internal surface of a tubular member, such as a pipe. In particular the apparatus uses an inspection head which travels in a helical path while magnetizing regions of the internal surface of a tubular member and detecting the magnetic flux leakage created by substantially all flaws. The invention can include a computer based system which is used to store, analyze, and display data as well as to control the other functions of the device. Thus, the location and severity of flaws on or near the internal surface of a tubular member can be accurately determined and recorded.

Figures 1, 2, 3, 4:
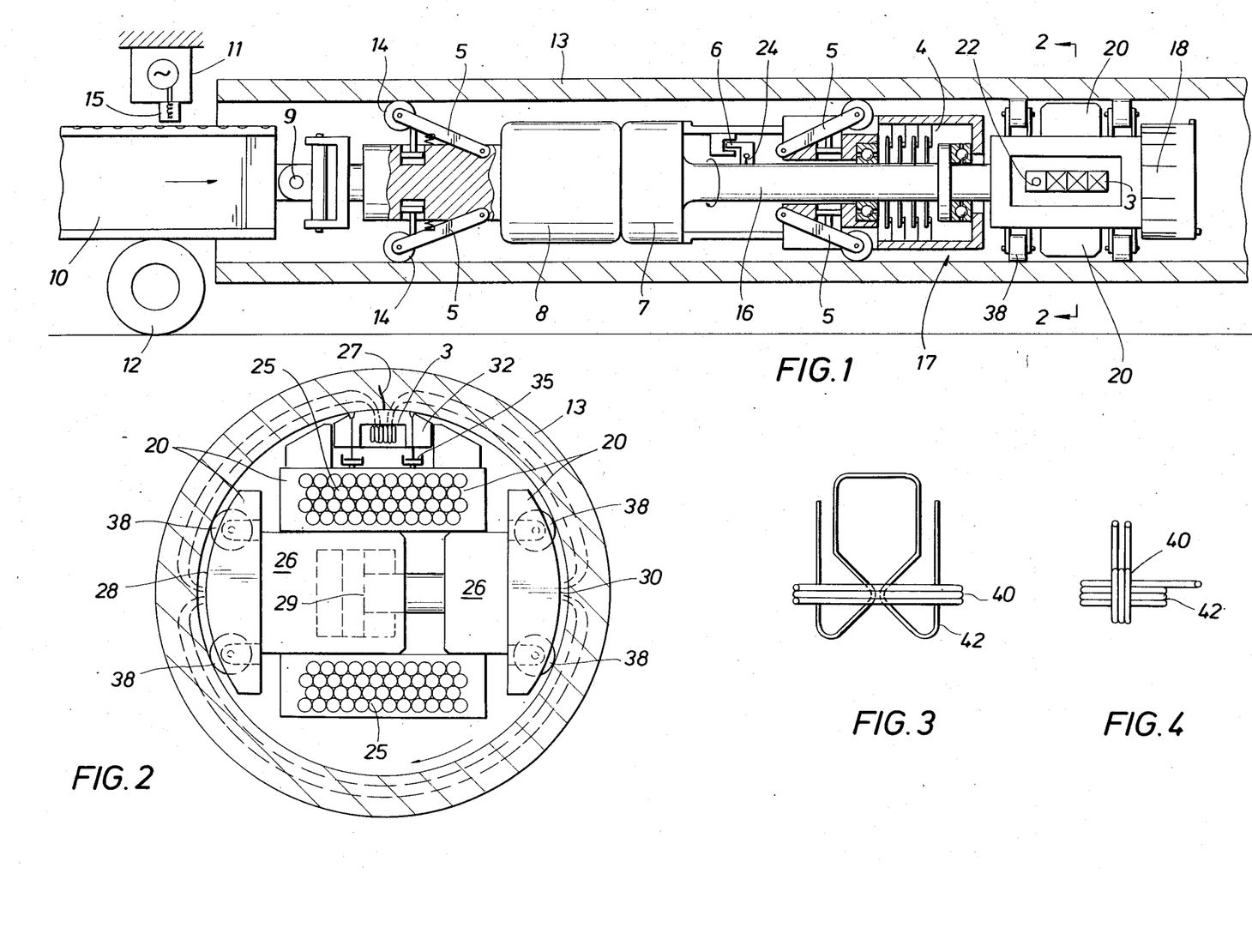
FIG. 1 is a longitudinal, cross-sectional view of the inspection head apparatus of the invention as it enters a tubular member.
FIG. 2 is a tranverse cross-sectional view of the preferred embodiment of the tubular inspection device, showing an electromagnet and the magnetic flux leakage sensor system which are independently actuated radially with respect to the internal surface of the tubular member.
FIG. 3 is a planar view of two channels of a typical sensor coil arrangement.
FIG. 4 is an elevational view of two channels of a typical sensor coil arrangement.

FIG. 1 is a longitudinal, cross-sectional view of the tubular inspection apparatus of the invention as it enters the bore of tubular member 13. Inspection head 17 begins at universal joint 9. Drive beam 10 is attached to inspection head 17 by universal joint 9 and propels inspection head 17 longitudinally through tubular member 13. Drive beam 10 contains position markings which can be monitored by at least one longitudinal position sensor 15 attached to longitudinal encoder 11, which is located adjacent to the drive beam to determine the position of inspection head 17 in relation to the longitudinal axis of tubular member 13. A longitudinal motion motor (not shown in FIG. 1) powers friction drive wheels 12 which allow drive beam 10 to move inspection head 17 through the bore of tubular member 13. Inspection head 17 includes electromagnet 20 which magnetizes tubular member 13 circumferentially as inspection head 17 rotates along a helical path. At least one magnetic flux leakage sensor 3 reads the magnetic flux created by any defect detectable from the bore of tubular member 13. Electronic unit 18, also a part of inspection head 17, processes signals detected by magnetic flux leakage sensor 3. Shaft 16 rotates the portion of inspection head 17 containing electromagnet 20, magnetic flux leakage sensor 3, and electronic unit 18. The rotation of shaft 16 is powered by motor 8 through speed reducer 7. The rotational speed is selected so that, as inspection head 17 is driven longitudinally through tubular member 13, the magnetizing circuit and magnetic flux leakage sensor 3 follow a helical path that covers substantially the entire internal surface of tubular member 13.

Other mechanisms are present in inspection head 17. Slip ring system 4 transfers electrical power to and from electromagnet 20, electronic unit 18, and magnetic flux leakage sensor 3. Accelerometer 22, located adjacent to magnetic flux leakage sensor 3, is used to detect any variations from the expected circumferential acceleration of magnetic flux leakage sensor 3, which would produce unwanted signals. These variations may result from magnetic flux leakage sensor 3 impacting obstructions or irregularities on the internal surface of tubular member 13. Accelerometer 22 produces a signal output which is recorded and can be plotted along with magnetic flux leakage. The accelerometer signal output can be used by a human operator or compared with calculations made by a data acquisition system to determine if irrelevant signals are present that should be ignored. Azimuthal encoder 6 determines the circumferential position of shaft 16 at all times during the inspection process. Reference pendulum 24 is suspended within azimuthal encoder 6, giving a gravitational reference point by which the circumferential location of the rotating section of inspection head 17 can be determined at all times. Inspection head 17 is centralized by multiple linkage support-arm, pneumatic piston-actuated assemblies 5 which are mounted to the non-rotating section of inspection head 17. Rubber wheels 14 are attached to each assembly 5 to maintain contact with the internal surface of tubular member 13. Assemblies 5 are adjustable so that inspection head 17 can be centralized in tubular members of varying sizes.

Substantially the entire internal surface of tubular member 13, with the exception of a few inches at each end, is inspected without rotation and translation of tubular member 13.

FIG. 2 is a cross-sectional view of inspection head 17 shown in a plane perpendicular to the longitudinal axis of tubular member 13, along line 2—2 of FIG. 1, showing electromagnet 20 and magnetic flux sensor 3. To begin the inspection process, pneumatic power is supplied to each assembly 5 to centralize inspection head 17 and then electrical power is supplied to slip ring system 4, which in turn supplies electromagnet 20 with preferably direct current. The current enters electrical coil 25 and induces a magnetic field in ferrous core 26 of electromagnet 20, which in turn induces a magnetic field in tubular member 13. Substantially the entire internal surface of tubular member 13 is magnetized, with magnetic poles at locations 28 and 30.

Nonmagnetic wear shoe 32 is positioned between locations 28 and 30, in which magnetic flux leakage sensor 3, located in a plastic matrix, is mounted. Shoe 32 prevents wear of sensor 3. Shoe 32 preferably is constituted of a thin layer of chrome or a similar metal plated over a soft bearing type metal, such as brass. Air flow is directed through small holes in wear shoe 32 by a pneumatic power source 33 (not shown in FIG. 2) through an air swivel 34 (not shown in FIG. 2) to establish a thin air cushion to reduce wear and friction.

Sensor 3 must remain in close proximity to tubular member 13 in order to reliably detect signals. Spring-piston-linkage assembly 35 is attached to wear shoe 32 in order to control lift-off, as well as to reduce rotational torque. Spring-piston-linkage assembly 35 and air piston 29, combined with a constant air flow rate, cause electromagnet 20 and wear shoe 32 to remain at a selected distance from tubular member 13. Rollers such as 38 supply radial support to the rotating section of inspection head 17.

FIG. 3 is a planar view of sensor 3 as it appears in a preferred embodiment of the invention. FIG. 4 is an elevational view of the sensor shown in FIG. 3. The system consists of at least one set of channels each of a 45° sensor coil 42 and a 0° sensor coil 40. The 45° sensor coil 42 consists of two triangular shaped windings connected in series and is positioned so that it is most sensitive to defects lying ±45° from the longitudinal axis of tubular member 13. This configuration also has the benefit of excluding background noise resulting from minor inherent imperfections in tubular member 13. If the defect is parallel to the longitudinal axis of tubular member 13, one of the triangular windings will detect a weak positive signal, while the other winding will detect a weak negative signal. Thus, the signals will cancel each other when the defect lies exactly parallel to the longitudinal axis.

The 0° sensor coil 40 is then wound on top of 45° sensor coil 42 in a "stand-up" coil position. The 0° sensor coil 40 is most sensitive to defects lying parallel to the longitudinal axis of tubular member 13. The 0° sensor coil 40 is accurate on defects with orientations ranging from parallel to the longitudinal axis to ±22° from the longitudinal axis of tubular member 13. The 45° sensor coil 42 will be most accurate in defects ranging from ±22° to ±67° from the longitudinal axis.

Figure 5:
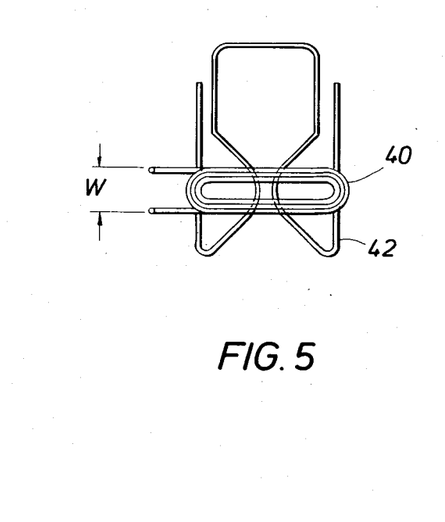
FIG. 5 is a planar view of an alternate embodiment of two channels of a sensor coil arrangement.
Figure 6:
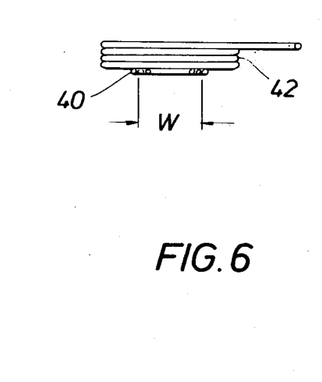
FIG. 6 is an elevational view of the sensor coil arrangement of FIG. 5.

The 0° sensor coil 40 may also be wound in the plane of 45° sensor coil 42, as shown in FIGS. 5 and 6. This is referred to as a "pancake" coil position. FIG. 5 shows a planar view and FIG. 6 shows an elevational view of the pancake coil position. The 0° sensor coil 40, when wound in this plane is very sensitive to circular defects. In addition, the geometry of the sensor coil may be optimized to improve the signal to background noise ratio. The most desirable 0° sensor coil widths range from 0.070 inch to 0.125 inch, based on experiments.

In all cases, 0° sensor coil 40 and, to a lesser degree, 45° sensor coil 42, will pick up background signals due to magnetic flux leakage caused by minor imperfections such as surface roughness. Electronic filters 44 positioned in electronic unit 18 of FIG. 1 will eliminate some of the background signals. The remainder will be eliminated by the control-data acquisition system by using stored threshold settings, as described in more detail later.

As tubular member 13 is magnetized, the magnetic field lines will extend generally circumferentially along the internal surface of tubular member 13. If there is a defect along this surface such as defect 27 of FIG. 2, the magnetic field lines will extend generally perpendicularly to or radially from the internal surface of tubular member 13 at that point. Sensor 3 will produce a voltage signal indicative of such perpendicular or radial component of the magnetic field at such point.

Figure 7:
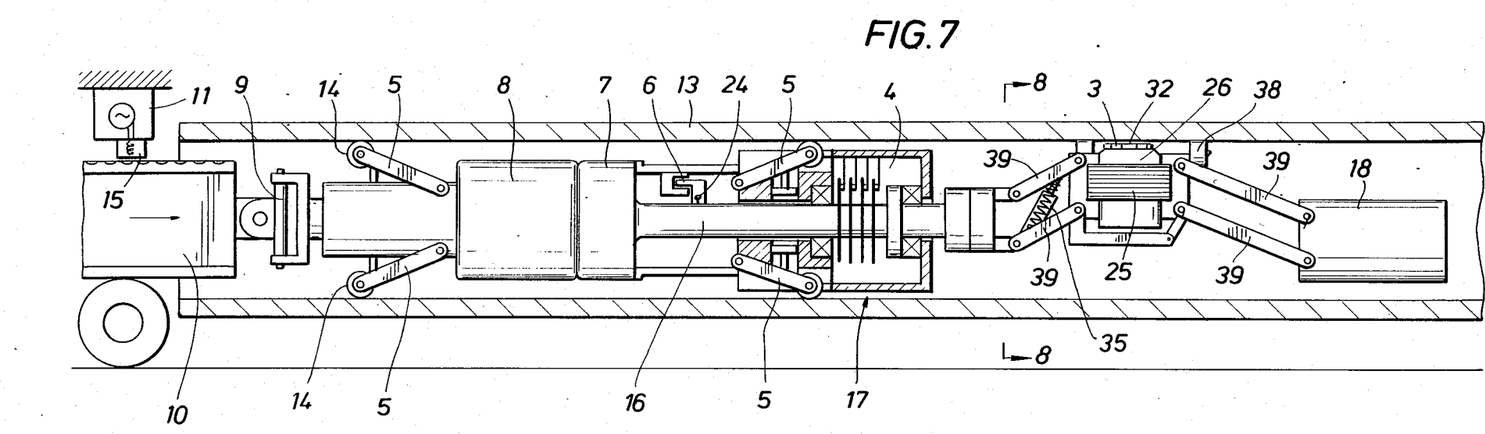
FIG. 7 is a longitudinal view of the alternate embodiment of the inspection head apparatus in which a spring-piston-linkage assembly is used to radially actuate the electromagnet and magnetic flux leakage sensor, eccentrically against a small area of a pipe bore.
Figure 8:
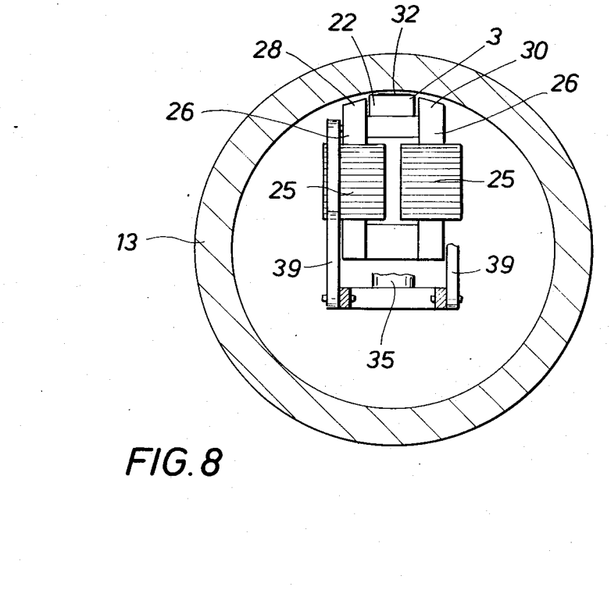
FIG. 8 is a transverse cross-sectional view of the inspection head apparatus of FIG. 7.

An alternate embodiment of the system may be preferred for inspecting tubular members having large internal diameters, for example, in excess of 5.5 inches of bore. This embodiment will be described with reference to FIG. 7 and FIG. 8. FIG. 7 is a longitudinal view of the inspection head of the alternate embodiment. FIG. 8 is a transverse cross-sectional view of the inspection head apparatus of FIG. 7 at line 8—8. Electromagnet 20 is comprised of two electrical coils 25 and a ferrous core 26. A magnetic flux field is then generated between poles 28 and 30. The system operates in this embodiment essentially in the same manner as the previously discussed embodiment. However, only the surface between poles 28 and 30 is magnetized. Sensor 3 detects defects in the same manner. A single spring-piston-linkage assembly 35 is required since electromagnet 20 and magnetic flux leakage sensor 3 are fixed together. Also, piston linkage network 39 is used to eccentrically position electromagnet 20 near the bore. Piston linkage network 39 is adjustable to enable the apparatus to accommodate a wide variety of pipe bores. For example, by use of a single linkage network, a range of pipe bores from six inches to ten inches of diameter can be accommodated.

Figure 9A:
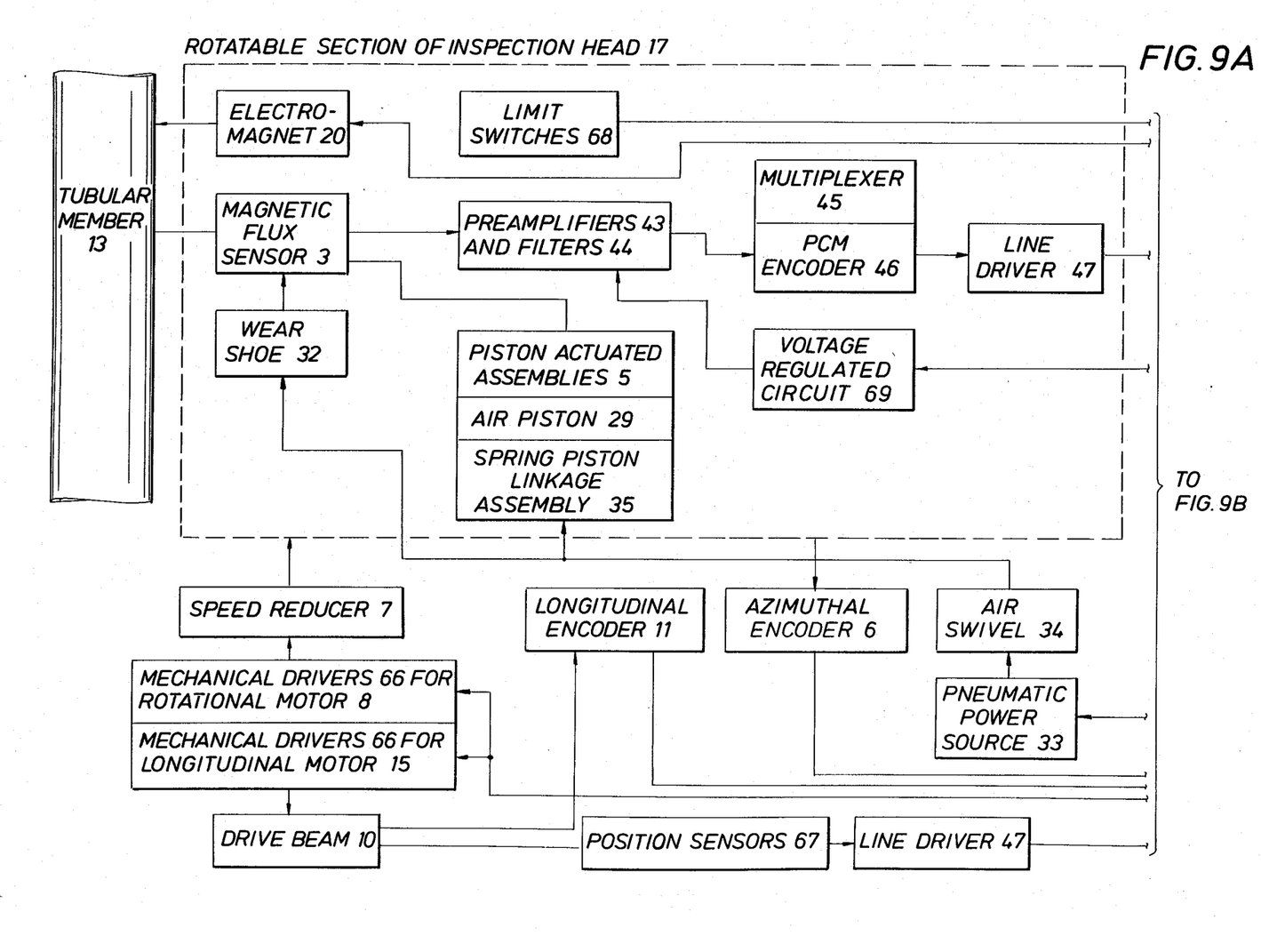
FIGS. 9A and B together are a block diagram of the electro-mechanical subassemblies of the tubular inspection device of the invention, indicating activities performed as inspection is carried out.
Figure 9B:
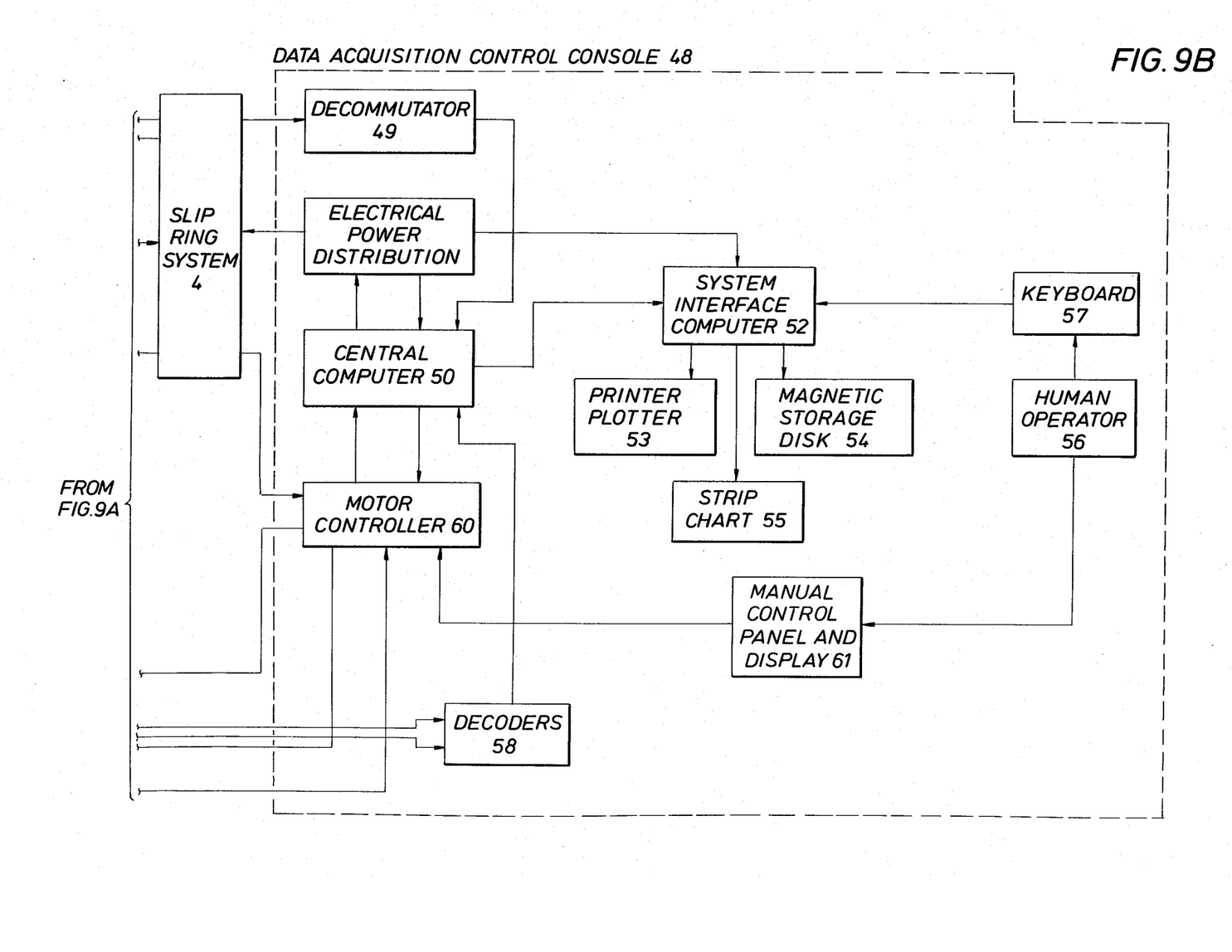

FIG. 9 is a block diagram of the tubular inspection device of the invention as inspection is carried out. Each channel of sensor system 3 sends its signals to the electronic circuits in inspection head 17, which contains preamplifiers 43 and filter system 44, multiplexer 45, pulse code modulator ("PCM") encoder 46, and line driver 47. Data is transferred to preamplifier 43 and filter system 44, which boosts and filters the signal, thereby eliminating some background noise. The data is encoded and digitized by multiplexer 45 and PCM encoder 46. Voltage regulation circuits 69 facilitate the operation of all electronic components. The data is sent through line driver 47, slip ring assembly 4, and to a control data acquisition console 48. Decommutator 49, preferably an Intel Model 7102, separates the data so that the data from each channel is individually readable. The data is then supplied to central computer 50, which is preferably a high speed data acquisition computer such as an Intel SBC 86/05. Central computer 50 processes data received from PCM encoder 46 via decommutator 49. The processed data is sent to system interface computer 52, which is suitably a Hewlett Packard minicomputer HP-9915. Interface computer 52 may be attached to printer/plotter 53, magnetic storage disk 54, and/or strip chart recorder 55 to provide output in readable form. Interface computer 52 also allows input from human operator 56 via an input device such as keyboard 57. The final output may be displayed as an alpha-numeric table with descriptive header information or as an analog strip chart record. Algorithms in central computer 50 convert the raw digitized signal data into a reduced or summarized form by calculating peak-to-peak voltage, signal frequency, and defect depth estimations. This converted data is then displayed by the system interface computer 52 via the previously described output options. Human operator 56 can select the desired output options.

Azimuthal encoder 6 sends data as to the azimuthal position of the inspection head to central computer 50 via decoder 58. Longitudinal encoder 11 also sends data regarding the position of inspection head 17 in relation to the longitudinal axis of tubular member 13.

Central computer 50 uses an algorithm stored in its programmable, read-only-memory (PROM), in conjunction with preset parameters in its random-access-memory (RAM) to process the signal data received from sensor 3. As the signal data is acquired, its value is compared against stored threshold values, which are programmed values set at levels greater than expected background noise. For example, if 45° sensor coil 42 detects a signal which exceeds the stored threshold value for that signal, that signal data will be retained, along with simultaneously collected data from azimuthal encoder 6 and longitudinal encoder 11. Central computer 50 makes all necessary calculations and transfers them, via a communications channel such as an RS-232-C, to system interface computer 52.

Central computer 50 is also linked to motor controller 60, containing its own separate central processing unit and binary counter, through a bidirectional interface. Motor controller 60 regulates manual control panel and display 61, a longitudinal position counter and display, an azimuthal position counter, a system electronic logic sequence control, and limit switch circuitry.

Human operator 56 can manually operate motor controller 60 via a push button system located on manual control panel and display 61. Central computer 50 can automatically control operations by using information stored in its random access memory (RAM). Manual control panel and display 61 includes mechanisms allowing manual control of functions such as operation of electromagnet mode selection, longitudinal speed, longitudinal direction, an on/off switch for electromagnet 20, and an on/off switch for data acquisition.

Motor controller 60 controls longitudinal and rotational mechanical drivers 66 to select longitudinal and rotational speed of inspection head 17, as well as longitudinal direction. Mechanical drivers are in contact with drive beam 10 and shaft 16. Information on the longitudinal position of inspection head 17 is sent to motor controller 60 via longitudinal encoder 11, which is mounted proximal to drive beam 10, and azimuthal encoder 6. Longitudinal encoder 11 is comprised of two eddy current sensors which detect equidistantly spaced slots in drive beam 10. An electronic signal is sent to a longitudinal position counter and display, which counts the number of pulses induced by the slots. Longitudinal encoder 11 is used to send data regarding the position of inspection head 17 in relation to the longitudinal axis of tubular member 13.

Azimuthal encoder 6 is comprised of a group of optical sensors which detect lines on a disc attached to shaft 16. Electronic pulses are generated and counted by an azimuthal position counter as lines pass the optical sensors. A reference pendulum 24 is suspended within azimuthal encoder 6 to maintain a stationary position with respect to the earth's gravitational field.

Motor controller 60 also sends status information to central computer 50 regarding the functions it controls, including magnet on/off, longitudinal drive forward/reverse, inspection mode automatic/manual, inspection run/stop, data in storage/not in storage, and data acquisition on/off. Position sensors 67 send information via line drivers 47 to motor controller 60 regarding the position of inspection head 17 at the start of inspection, whether inspection head 17 is properly coupled to tubular member 13, and when inspection head 17 is being stored. Limit switches 68 are connected to motor controller 60 via slip ring system 4. Limit switches 68 include switches for reversing the inspection head's direction when the end of a pipe is reached or when a mechanical obstruction is detected. Central computer 50 sends status information to motor controller 60 such as the availability of memory and whether the system is ready to accept data.

Figure 10:
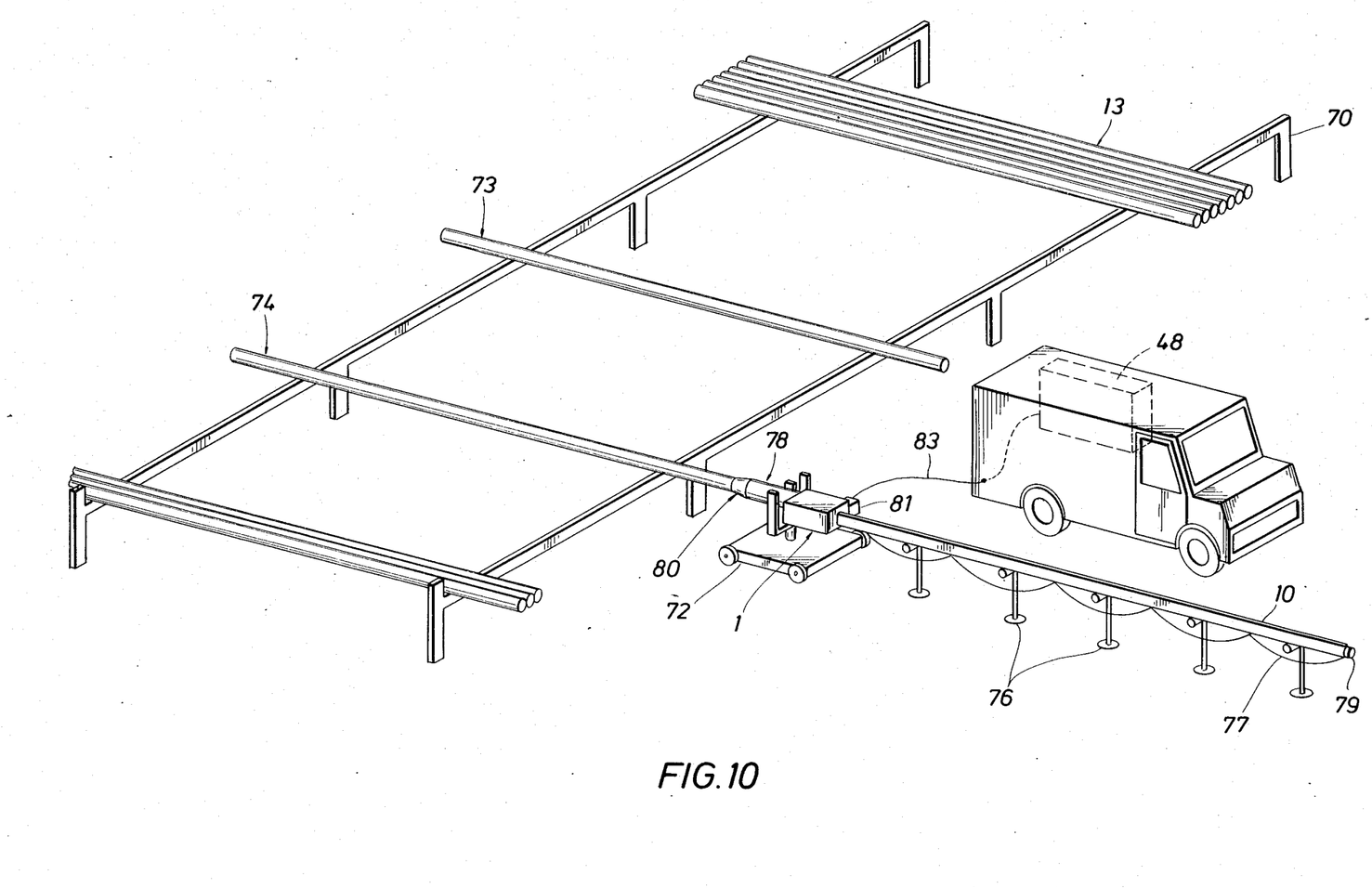
FIG. 10 is a perspective view of the tubular inspection apparatus of the invention, with a rack on which a plurality of pipes are positioned, illustrating the manner in which the inspection device is expected to be used in practice.

FIG. 10 shows the apparatus of the invention as it is intended for use in practice. Tubular members 13 are kept on rack 70 which has stations for storage, cleaning, and inspection. The internal surfaces of tubular members 13 are first cleaned at cleaning station 73 and then inspected. Tubular inspection apparatus 1 is placed on support cart 72 at inspection station 74. Drive beam 10 rests on beam support 76. Data acquisition control console 48, is in immediate proximity to tubular inspection apparatus 1.

Electrical cable 77 includes electrical lines for the transmission of data and power. Cable 77 is suspended from the first end of drive beam 10 in inspection head 17 to the second end of drive beam 10, where electrical end connection 79 is located. Junction box 81 connects tubular inspection apparatus 1 via transmission lines 83 to data acquisition control console 48 and all related control apparatus.

Inspection head 17 is stored in storage tube 78 until inspection begins. To begin inspection, a first end of adapter 80 is attached to a first end of tubular member 13. A second end of adapter 80 is attached to storage tube 78, whereby tubular inspection apparatus 1 is accessed to tubular member 13.

This invention has significant advantages over the prior art. The device collects signals as to the existence of a defect. The control-data acquisition system is capable of analyzing and processing these signals so that the severity of the defect, as well as its axial and circumferential location can be accurately determined. The computer allows for the operator to input a specific pipe identification label with its corresponding inspection scan. This eliminates the need for detailed and costly manual inspection prior to repair. Signals having values less than the programmed threshold value stored in central computer 50 are eliminated. In addition, the final output is an alpha-numeric table of digitized data with descriptive headings that can be readily understood. Output is also available as the conventional strip chart record. Permanent records can be maintained by the magnetic disks.

The invention also is capable of being adapted to inspect tubulars with a variety of pipe bores. A spring-piston-linkage assembly 35 can be inserted in inspection head 17 so that electro-magnet 20 and wear shoe 32 are maintained a selected distance from the internal surface of tubular member 13. The alternate embodiment, which only magnetizes a portion of the tubular member wall, is advantageous for inspecting a variety of tubular member bores as well as larger diameter bores. Further, the internal bore is magnetically energized to a sufficient level so that defects within thick walled tubulars (e.g., over one inch wall thickness) can be detected. A magnetic flux leakage can be detected which is created by flaws on or near the internal bore of tubular member 13.

Inspection head 17 has a lightweight construction and has a self-contained rotational motor. A relatively small longitudinal motor and small friction wheels are sufficient to provide axial movement resulting in a helical scan covering substantially the entire internal surface area of tubular member 13. The system eliminates the need to rotate or translate large, heavy tubular members, resulting in a safer, more energy efficient inspection operation than found in the prior art.

The principle of the invention and the best mode contemplated for applying that principle have been described. It is to be understood that the foregoing is illustrative only and that other means and techniques can be employed without departing from the true scope of the invention defined in the following claims.

We claim:

1. An apparatus for detecting defects on or near the internal surface of a tubular member, including:
    an inspection head sized so as to be insertable into the bore of the tubular member, said inspection head including an electromagnet capable of creating at least one generally circumferential magnetic flux between two magnetic poles, at least one magnetic flux leakage sensor positioned between said magnetic poles coplanar with said electromagnet, and a first rotational motor connected to said electromagnet and to said magnetic flux leakage sensor, said electromagnet and said magnetic flux leakage sensor being rotatable about a helical path within said tubular member;
    a drive beam attached to a longitudinal motion motor and to said inspection head for moving said inspection head bidirectionally along the longitudinal axis of said tubular member;
    an azimuthal encoder attached to said inspection head for determining the circumferential position of said inspection head in said tubular member;
    a longitudinal encoder located adjacent to said drive beam for determining the position of said inspection head in relation to the longitudinal axis of said tubular member;
    a signal transmission system attached to said magnetic flux leakage sensor, said azimuthal encoder, and said longitudinal encoder for transmitting signals from said magnetic flux leakage sensor, circumferential position signals, and longitudinal position signals; and
    a control-data acquisition system capable of receiving signals from said signal transmission system for correlating signal data from said magnetic flux leakage sensor to an axial and a circumferential position on the internal surface of said tubular member.

2. The apparatus of claim 1 further including a nonmagnetic wear shoe attached to said inspection head and to said magnetic flux leakage sensor.

3. The apparatus of claim 2 further including a spring-piston-linkage assembly, an air piston, an adjustable piston linkage network, and one or more rollers attached to said inspection head to which said wear shoe is attached so that said electromagnet and said magnetic flux leakage sensor remain spaced a selected distance from the internal surface of said tubular member.

4. The apparatus of claim 1 wherein said magnetic flux leakage sensor includes a first sensor coil shaped substantially as two triangular windings connected in series and positioned to be most sensitive to defects lying ±45° from the longitudinal axis of said tubular member, and a second coil positioned to be sensitive to defects lying substantially along the longitudinal axis to ±22° from the longitudinal axis of said tubular member.

5. The apparatus of claim 4 wherein said first sensor coil and said second sensor coil are wound in a stand-up coil position.

6. The apparatus of claim 4 wherein said first sensor coil and said second sensor coil are wound in a pancake coil position.

7. The apparatus of claim 1 wherein said longitudinal encoder includes at least one longitudinal position sensor.

8. The apparatus of claim 1 further including a plurality of support arm assemblies attached to said inspection head, said assemblies capable of being expanded or contracted radially.

9. The apparatus of claim 1 wherein said signal transmission system includes an electronic unit attached to said magnetic flux leakage sensor, said electronic unit capable of receiving signals from said magnetic flux leakage sensor, encoding said signals, and further capable of transmitting said encoded signals to a control-data acquisition system.

10. The apparatus of claim 9 wherein said electronic unit includes a preamplifier to boost the signals received from said sensors, one or more filters to eliminate background noise, a multiplexer and pulse code modulator encoder system to encode and digitize the signals, and a line driver attached to said transmission system.

11. The apparatus of claim 1 further including an accelerometer to detect variations from the expected acceleration of said inspection device.

12. An apparatus for detecting defects on or near the internal surface of a tubular member, including:
    an inspection head sized so as to be insertable into the bore of the tubular member, said inspection head including an electromagnet capable of creating at least one generally circumferential magnetic flux between two magnetic poles, at least one magnetic flux leakage sensor positioned between said magnetic poles coplanar with said electromagnet, and a first rotational motor connected to said electromagnet and to said magnetic flux leakage sensor, said electromagnet and said magnetic flux leakage sensor being rotatable about a helical path within said
    a longitudinal motion motor;
    a drive beam attached to said longitudinal motion motor and to said inspection head for moving said inspection head bidirectionally along the longitudinal axis of said tubular member;
    an azimuthal encoder attached to said inspection head for determining the circumferential position of said inspection head in said tubular member;
    a longitudinal encoder located adjacent to said drive beam for determining the longitudinal position of said inspection head in relation to the longitudinal axis of said tubular member;
    a control-data acquisition system connected electronically to said inspection head for receiving and processing signal data detected by said magnetic flux leakage sensor and signal data produced by said longitudinal encoder and said azimuthal encoder, said control-data acquisition system also for correlation of all magnetic flux leakage sensor signal data to an axial and a circumferential position on the internal surface of said tubular member, said control-data acquisition system capable of storing, recording, and displaying all signal data; and a motor controller attached to said control-data acquisition system, said inspection head, said azimuthal encoder, and said longitudinal encoder, said motor controller regulated by said control-data acquisition system to direct the longitudinal motion of said inspection apparatus and the rotational motion of said inspection head so that said electromagnet and said magnetic flux leakage sensor are driven around a helical path within said tubular member.

13. The apparatus of claim 12 where said control-data acquisition system includes a high speed central computer and a system interface computer.

14. An apparatus for detecting defects on or near the internal surface of a tubular member, including:

an inspection head sized so as to be insertable into the bore of a tubular member, said inspection head including an electromagnet capable of creating at least one generally circumferential magnetic flux between two magnetic poles, a spring-piston-linkage assembly, at least one magnetic flux leakage sensor positioned between said magnetic poles coplanar with said electromagnet, and a rotational motor connected to said electromagnet and said magnetic flux leakage sensor;

a drive beam attached to said longitudinal motion motor and to said inspection head for bidirectional movement of said inspection head along the longitudinal axis of said tubular member;

a longitudinal encoder for determining the longitudinal position of said inspection head within said tubular member;

a longitudinal motor reversing relay for reversal of the direction of longitudinal movement of said inspection head;

an azimuthal encoder attached to said inspection head for determining the circumferential position of said inspection head in said tubular member;

a control-data acquisition system comprising a high speed central computer and a system interface computer, said control-data acquisition system electronically connected to said inspection head for receiving and processing signal data detected by said magnetic flux leakage sensor, said longitudinal encoder and said azimuthal encoder, and for correlation of all magnetic flux sensor signal data to an axial and a circumferential position on the internal surface of said tubular member, said control-data acquisition system capable of storing, recording, and displaying said signal data; and a motor controller unit including a central processing unit for controlling the functions of said rotational motor, said longitudinal motion motor, said longitudinal motor reversing relay, and said spring-piston-linkage assembly, said motor controller regulated by said control-data acquisition system via a bidirectional interface.

15. The apparatus of claim 14 wherein said control-data acquisition system further includes an input device to allow manual control of all functions.

16. The apparatus of claim 14 wherein said control-data aquisition system further includes at least one limit switch and at least one position sensor connected to said motor controller to automate all mechanical functions of the apparatus.

17. An apparatus for detecting defects on or near the internal surface of a tubular member, including:

an inspection head insertable into the bore of the tubular member, said inspection head including a direct current electromagnet capable of creating at least one generally circumferential magnetic flux between two magnetic poles, at least one magnetic flux leakage sensor positioned between such magnetic poles, a nonmagnetic wear shoe, a spring-piston-linkage assembly attached to said wear shoe, a piston linkage network, at least one roller, and a rotational motor, saiu electromagnet and said magnetic flux leakage sensor supported in the same plane with each other at a selected distance from the internal surface of said tubular member by said spring-piston-linkage assembly and said piston linkage network while said roller is driven around a helical path within said tubular member:

a longitudinal motion motor;

a drive beam attached to said longitudinal motion motor and to said inspection head for moving said inspection head bidirectionally along the longitudinal axis of said tubular member with drive mechanisms located external to the tubular member;

an azimuthal encoder attached to said inspection head for determining the circumferential position of said inspection head in said tubular member;

a longitudinal encoder for determining the position of said inspection head in relation to the longitudinal axis of said tubular member;

a control-data acquisition system electronically connected to said inspection head for receiving and processing signal data detected by said magnetic flux leakage sensor, and produced by said longitudinal encoder and said angular encoder, and also for correlation of all signal data to an axial and circumferential position on the internal surface of said tubular member, said control-data acquisition system also capable of storing, recording, and displaying all signal data;

a motor controller unit including a central processing unit for controlling the functions of said rotational motion motor, said longitudinal motion motor, said spring-piston-linkage assembly, and said piston linkage network, said motor controller regulated by said control-data acquisition system via a bidirectional interface; and at least one limit switch and at least one position sensor connected to the motor controller to automate all mechanical functions of the apparatus.

18. The apparatus of claim 17 wherein said magnetic flux sensor includes a first sensor coil shaped substantially as two triangular windings connected in series and positioned to be most sensitive to defects laying $\pm 45°$ from the longitudinal axis of said tubular member, and a second coil positioned to be most sensitive to defects lying substantially along the longitudinal axis to $\pm 22°$ from the longitudinal axis of said tubular member.

19. The apparatus of claim 17 further including an accelerometer to detect variations from the expected acceleration of the rotating section of said inspection head.

20. The apparatus of claim 17 further including a longitudinal motor reversing relay for reversal of the direction of longitudinal movement of said inspection head, said reversing relay controlled by said motor controller unit.

21. A method of detecting defects on or near the internal surface of a tubular member, which comprises:
   deploying an inspection head within said tubular member, said inspection head including an electromagnet capable of creating at least one generally circumferential magnetic flux between two magnetic poles, at least one magnetic flux leakage sensor positioned between said magnetic poles coplanar with said electromagnet, and a rotational motor connected to said electromagnet, and a rotational motor connected sensor;
   rotating the section of inspection head including said electromagnet and said magnetic flux leaking sensor while moving said inspection head forward along the longitudinal axis of said tubular member so that said rotating section is driven around a helical path within said tubular member;
   creating a generally circumferential magnetic flux between said two magnetic poles on and near the internal surface of said tubular member adjacent to said rotating section during rotation;
   detecting said magnetic flux leakage signals using said magnetic flux leakage sensor;
   measuring the circumferential position of said inspection head in said tubular member using an azimuthal encoder attached to said inspection head;
   measuring the position of said inspection head in relation to the longitudinal axis of said inspection head using a longitudinal encoder; and
   correlating each said magnetic flux leakage signal to an axial and a circumferential position on the internal surface of said tubular member.

22. The method of claim 21 further comprising maintaining said electromagnet and said magnetic flux leakage sensor a selected distance from the internal surface of said tubular member by use of a nonmagnetic wear shoe attached to a spring-piston-linkage, said electromagnet, and said magnetic flux leakage sensor, and at least one roller for controlling lift-off and reducing rotational torque of said inspection head.

23. The method of claim 21 further comprising the positioning of said magnetic flux leakage sensor so that each sensor includes a first sensor coil shaped substantially as two triangular windings connected in series and most sensitive to defects lying ±45° from the longitudinal axis of said tubular member, and a second coil most sensitive to defects lying substantially along the longitudinal axis of said tubular member.

24. The method of claim 21 further comprising expanding or contracting radially a plurality of support arm assemblies attached to said inspection head so that inspection head may be used in a variety of bore sizes.

25. The method of claim 21 further comprising the transmittal of said magnetic flux leakage signal data, said longitudinal position signal data, and said longitudinal position signal data by an electronic unit attached to said sensors, which receives, encodes, and transmits to a control-data acquisition system all signal data.

26. The method of claim 25 further comprising boosting of the signals received from said sensors by a preamplifier, eliminating background noise by one or more filters, encoding and digitizing the signals by a multiplexer and pulse code modulator encoder system, and facilitating transmission of said signals by a line driver attached to said electronic unit.

27. The method of claim 21 further comprising detection of variations from the expected acceleration of said inspection head using an accelerometer attached to said inspection head.

28. A method of detecting defects on or near the internal surface of a tubular member, which comprises:
   deploying an inspection head within said tubular member, a section of said inspection head including an electromagnet capable of creating at least one generally circumferential magnetic flux between two magnetic poles, at least one magnetic flux leakage sensor positioned between said magnetic poles coplanar with said electromagnet, and a rotational motor connected to said electromagnet and said magnetic flux leakage sensor;
   rotating the section of inspection head including said electromagnet and said magnetic flux leakage sensor while moving said inspection head forward along the longitudinal axis of said tubular member using a longitudinal motion motor and at least one friction drive wheel located external to the tubular member so that said rotating section is driven around a helical path within said tubular member;
   creating a generally circumferential magnetic flux between two magnetic poles on or near the internal surface of said tubular member adjacent to said rotating section during rotation;
   detecting said magnetic flux leakage signals using said magnetic flux leakage sensor;
   measuring the azimuthal position of said inspection head in said tubular member using an azimuthal encoder attached to said inspection head;
   measuring the position of said inspection head in relation to the longitudinal axis of said inspection head using a longitudinal encoder;
   transmitting magnetic flux leakage signal data, azimuthal position signal data, and longitudinal position signal data to a control data acquisition system capable of receiving and processing said signal data, and for correlation of all signal data to an axial and a circumferential position on the internal surface of said tubular member; and
   directing the longitudinal motion of said inspection device and the rotational motion of said electromagnet and said magnetic flux leakage sensor by a motor controller unit regulated by said control-data acquisition system so that said electromagnet and said magnetic flux leakage sensor are driven around a helical path within said tubular member so that substantially the entire internal surface of said tubular member is inspected.

29. The method of claim 28 further comprising comparing the value of signal data acquired from said magnetic flux leakage sensor with stored threshold values in said control-data acquisition system and retaining only the magnetic flux leakage signal data which exceeds said threshold values.

30. The method of claim 29 further comprising storing, recording, and displaying magnetic flux leakage signal data, azimuthal position signal data, and longitudinal position signal data by use of said control-data acquisition system.

31. A method of detecting defects on or near the internal surface of a tubular member which comprises:

deploying an inspection head within the tubular member, said inspection head including an electromagnet capable of creating at least one generally circumferential magnetic flux between two magnetic poles, at least one magnetic flux leakage sensor positioned between said magnetic poles, a nonmagnetic wear shoe, a spring-piston-linkage assembly attached to said wear shoe, and at least one roller, said electromagnet and said magnetic flux leakage sensor supported in the same plane with each other at a selected distance from the internal surface of said tubular member by said spring-piston-linkage assembly while said roller is driven around a helical path within said tubular rotating the section of said inspection head including said electromagnet and said magnetic flux leakage sensor while moving said inspection head forward along the longitudinal axis of said tubular member so that said rotating section is driven around a helical path within said inspection head;

creating a generally circumferential magnetic flux between two magnetic poles on and near the internal surface of said tubular member during rotation of the rotating section of said inspection head;

detecting said magnetic flux leakage signals by use of said magnetic flux leakage sensor;

measuring the azimuthal position of said inspection head in said tubular member by use of an azimuthal encoder attached to said inspection head;

measuring the position of said inspection head in relation to the longitudinal axis of said inspection head by use of a longitudinal encoder;

transmitting magnetic flux leakage signal data, azimuthal position signal data, and longitudinal position signal data to a control-data acquisition system for receiving and processing said signal data, and also for correlation of all signal data to an axial and a circumferential position on the internal surface of said tubular member.

32. The method of claim 31 further comprising the positioning of said magnetic flux leakage sensor so that each sensor includes a first sensor coil shaped substantially as two triangular windings connected in series and most sensitive to defects lying ±45° from the longitudinal axis of said tubular member, and a second coil most sensitive to defects lying exactly along the longitudinal axis of said tubular member.

33. The method of claim 31 further comprising detection of variations from the expected acceleration of said inspection head using an accelerometer attached to said inspection head.

34. The method of claim 31 further comprising controlling the functions of said rotational motor, said longitudinal motion motor, said longitudinal motor reversing relay, and said spring-piston-linkage assembly by a motor controller unit, said motor controller unit regulated by said control-data acquisition system via a bidirectional interface.

* * * * *